United States Patent [19]

Kurihara et al.

[11] Patent Number: 5,108,739

[45] Date of Patent: Apr. 28, 1992

[54] WHITE COLORED DEODORIZER AND PROCESS FOR PRODUCING THE SAME

[75] Inventors: Tokumitsu Kurihara; Tatsuo Saito; Hidefumi Harada, all of Yamaguchi, Japan

[73] Assignee: Titan Kogyo Kabushiki Kaisha, Ube, Japan

[21] Appl. No.: 541,207

[22] Filed: Jun. 21, 1990

Related U.S. Application Data

[63] Continuation of Ser. No. 238,306, Aug. 30, 1988, abandoned.

[51] Int. Cl.⁵ .............................................. A41B 13/02
[52] U.S. Cl. ........................... 424/76.1; 106/430; 106/449; 423/101; 423/622; 423/610; 424/76.3; 424/76.5; 424/76.7
[58] Field of Search .............. 424/76.1, 76.3, 76.5, 424/76.7; 106/8.8, 430, 449; 423/101, 610, 622

[56] References Cited

U.S. PATENT DOCUMENTS

| | | | |
|---|---|---|---|
| 2,350,047 | 5/1944 | Klarmann et al. | 424/68 |
| 3,383,231 | 5/1968 | Allan | 106/430 |
| 3,418,147 | 12/1968 | Fields | 106/430 |
| 3,961,037 | 6/1976 | Davies et al. | 423/656 |
| 4,088,736 | 5/1978 | Courty et al. | 423/230 |
| 4,128,630 | 12/1978 | Hayashi et al. | 424/69 |
| 4,187,282 | 2/1980 | Matsuda et al. | 423/244 |
| 4,297,233 | 10/1981 | Gualandi | 252/259.5 |
| 4,371,507 | 2/1983 | Farha, Jr. et al. | 423/230 |
| 4,440,668 | 3/1984 | Chang et al. | 502/331 |
| 4,492,769 | 1/1985 | Blanchard et al. | 502/262 |
| 4,725,415 | 2/1988 | Kidd | 423/230 |
| 4,777,034 | 10/1988 | Oliver et al. | 424/65 |

FOREIGN PATENT DOCUMENTS

| | | | |
|---|---|---|---|
| 5061926 | 5/1980 | Japan | . |
| 0203022 | 12/1982 | Japan | 502/350 |
| 0210848 | 12/1983 | Japan | 502/343 |
| 0110337 | 6/1985 | Japan | 502/343 |
| 216356 | 1/1987 | Japan | . |
| 3130136 | 6/1988 | Japan | . |
| WO81/01643 | 6/1981 | PCT Int'l Appl. | . |

*Primary Examiner*—Ellis P. Robinson
*Assistant Examiner*—Archene Turner
*Attorney, Agent, or Firm*—Fitch, Even, Tabin & Flannery

[57] ABSTRACT

A white colored deodorizer comprising titanium oxide and zinc oxide and a method for its preparation are disclosed.

2 Claims, No Drawings

WHITE COLORED DEODORIZER AND PROCESS FOR PRODUCING THE SAME

This application is a continuation of application Ser. No. 238,306 filed Aug. 30, 1988, now abandoned.

BACKGROUND OF THE INVENTION

The present invention relates to an agent for reducing the levels of odorous gases such as ammonia, mercaptans, amines and aldehydes. More specifically, the present invention relates to a novel deodorizer in white particulate form that contains as main ingredients titanium dioxide and zinc oxide, and which has very good adsorption characteristics.

Hydrogen sulfide, ammonia, mercaptans, amines, aldehydes and other odorous gases that are generated in daily life have caused an increasing amount of social concern about the deleterious effects they have on the biosphere and environment. In response to these concerns, a variety of deodorizers that are capable of reducing the target odorous gases have been proposed and put to practical use. Deodorizers for use in daily life have to satisfy the following minimal requirements:

(1) they must be capable of efficient reduction of the levels of hydrogen sulfide, ammonia, mercaptans, amines, aldehydes and other odorous gases that are generated in daily life;
(2) they must be safe to use;
(3) they must be easy to handle;
(4) they must be inexpensive; and
(5) they must offer a feeling of cleanliness.

However, none of the conventional deodorizers satisfy all of these requirements, nor do the most recently developed products. Activated carbon which is the most popular deodorizer in use today is highly effective in reducing mercaptans and amines but is not equally effective against hydrogen sulfide and ammonia which are typical of the odorous gases that are generated in daily life. In an attempt to solve this problem, a product has been developed that has an acid, an alkali or a certain halide supported on activated carbon. However, because of the use of an acid or alkali, this product requires very careful handling to avoid any danger to humans and hence is not suitable for daily use. Furthermore, the inherent black color of activated carbon limits the scope of use of deodorizers based on activated carbon.

Iron sulfate ($FeSO_4$) having L-ascorbic acid bound thereto is effective against basic odorous gases such as ammonia and amines but has little effect in reducing hydrogen sulfide, mercaptans and aldehydes. Furthermore, this product dissolves in water and hence is not suitable for the purpose of deodorizing wet gases.

Deodorizers classified as chemical odor modifiers are also available but many of them have strong acidity or alkalinity and the kinds of odorous gases that can be effectively controlled by these odor modifiers are limited. In addition, such deodorizers are sensitive to moisture and/or a dry atmosphere.

Organic deodorizers have low heat resistance, are difficult to process, and are expensive.

SUMMARY OF THE INVENTION

It is accordingly an object of the present invention to provide a novel deodorizer that is highly effective in reducing odorous gases generated in daily life such as ammonia, mercaptans, amines and aldehydes and which is safe and easy to handle.

This object of the present invention can be attained by a white colored deodorizer which is a white fine powder comprising coagulated particles of titanium dioxide and zinc oxide.

DETAILED DESCRIPTION OF THE INVENTION

The deodorizer of the present invention may be produced by the following procedures. A mixed aqueous solution of a water-soluble titanium compound and a water-soluble zinc compound is mixed with an alkaline aqueous solution by simultaneous addition into a certain medium in such a way that the combined solution will have a final pH of 6-12, preferably 7-9, thereby forming a white precipitate in the combined solution that is composed of titanium oxide, zinc oxide (ZnO), and bound water ($H_2O$). In the next step the precipitate is separated from the combined solution and dried.

Examples of the water-soluble titanium compound that can be used as a starting material for the production of the deodorizer of the present invention include titanium sulfate, titanyl sulfate, titanium chloride and titanium nitrate. Examples of the water-soluble zinc compound that can be used in the present invention in its second aspect include zinc sulfate, zinc chloride, zinc nitrate and zinc acetate.

The alkaline aqueous solution used for neutralizing the mixed aqueous solution may be selected from among aqueous solutions of sodium hydroxide, potassium hydroxide, magnesium hydroxide, calcium hydroxide, barium hydroxide, ammonia, etc. If the mixed aqueous solution contains a sulfate salt, aqueous solutions of calcium hydroxide and barium hydroxide are not desirably used since they will produce water-insoluble salts.

The water-soluble titanium compound and water-soluble zinc compound are mixed in such proportions that the molar ratio of $TiO_2$ to zinc oxide is within the range of 1:9 to 9:1, preferably from 3:7 to 7:3. If the molar ratio of $TiO_2$ to zinc oxide is smaller than 1:9 or greater than 9:1, the fine powder prepared from the resulting precipitate will display absorption characteristics similar to either pure zinc oxide or pure titanium dioxide. These characteristics are substantially inferior to those of the fine powder obtained in accordance with the compositional range specified by the present invention.

For the purposes of the present invention, it is essential that the mixed aqueous solution consisting of the water-soluble titanium compound and water-soluble zinc compound should be mixed with the aqueous alkaline solution in such a way that the resulting combined solution will have a final pH in the range of 6-12. At pHs below 6 or above 12, zinc hydroxide has high solubility in aqueous solutions and the efficiency of its precipitation is decreased. In the present invention, a mixed aqueous solution containing the water-soluble titanium compound and zinc hydroxide will co-precipitate with titanic acid to form hydroxides in the pH range of 6-12, the efficiency of precipitation is high enough to minimize the otherwise occurring deviation from the intended composition of the combined solution.

If the aqueous alkaline solution is slowly added to the mixed aqueous solution, or the mixed solution is slowly added to the aqueous alkaline solution, until the resulting combined solution has a final pH of 6-12, titanic acid and zinc hydroxide, which have different optimal pH regions for precipitation, will individually form separate particles and the powder that is obtained by drying them will be a mixture of pure $TiO_2$ and ZnO which does not have superior characteristics. The concentrations of the water-soluble titanium compound and the water-soluble zinc compound in the mixed aqueous solution are not limited to any particular values. However, from an industrial aspect, a high concentration is preferable.

When the mixed aqueous solution and the alkaline aqueous solution are mixed together to form a precipitate composed of $TiO_2$ and ZnO, a temperature in the range of 20°–80° C. may be employed, with the range of 40°–60° C. being preferred. After the precipitate has been filtered and washed, it may satisfactorily be dried at a temperature over the wide range of 100°–400° C., with the range of 120°–300° C. being preferred.

The deodorizer of the present invention which is based on the combination of $TiO_2$ and ZnO will experience a slight change in its adsorption characteristics if it is heated above 300° C. but it is sufficiently heat stable to maintain good characteristics even if it is heated up to about 400° C.

The white-colored deodorizer of the present invention which is based on the combination of $TiO_2$ and ZnO is capable of efficient reduction in the levels of hydrogen sulfide, ammonia, amines and other odorous gases that are generated in daily life. In addition, this deodorizer is safe to use since the $TiO_2$ and ZnO are nontoxic. Furthermore, the deodorizer is in a fine particulate form and can be readily supported on a carrier such as paper or other sheet materials. The deodorizer is thermally stable up to about 400° C. and can be worked into conventional plastics. In addition to the high potential of its industrial utility, the deodorizer of the present invention which is white in color is also suitable for use in cosmetics, sanitary products and disposable diapers.

The following examples are provided for the purpose of further illustrating the present invention but are not to be taken as limiting the scope thereof.

EXAMPLE 1

A 5-l beaker was charged with 1 l of pure water, which was heated at 60° C. with stirring. A mixed aqueous solution (2 l) of titanium sulfate (144 g as $TiO_2$) and zinc sulfate (16 g as ZnO) and an aqueous ammonia solution were simultaneously added dropwise to the pure water in the beaker over a period of 30 minutes with care being taken to ensure that the pH of the combined solution remained at 7.5. The resulting product was filtered, washed and dried at 200° C. for 3 hours to produce a white deodorizer of the $TiO_2$-ZnO-$H_2O$ system within the scope of the present invention. An X-ray diffraction analysis showed that this white deodorizer was amorphous. The BET specific surface area of the deodorizer was 410 $m^2/g$. The molar ratio of the deodorizer of $TiO_2$ to ZnO was 9.0:1.0.

The ability of this white deodorizer to adsorb odorous gases (i.e., hydrogen sulfide, ammonia, trimethylamine and ethyl mercaptan) was investigated by the following method. The white powder of the deodorizer (100 mg) was put into a glass vial having an inner capacity of 120 ml. After closing the vial with a rubber stopper, predetermined amounts of certain odorous gases were injected into the vial with a microsyringe. Two hours after the gas injection, the air in the vial was sampled with a microsyringe and the concentrations of the odorous gases in it were measured by gas chromatography. The results are shown in Table 1.

EXAMPLES 2-9

Eight kinds of white deodorizers of the $TiO_2$-ZnO-$H_2O$ system were prepared by repeating the procedures of Example 1 except that different quantities of titanium sulfate and zinc sulfate were added to form a mixed aqueous solution. The molar ratios of titanium sulfate to zinc sulfate used in each example are shown in Table 1.

The adsorption characteristics of the prepared deodorizers for various odorous gases are also shown in Table 1.

Comparative Example 1

A 5-l beaker was charged with 1 l of pure water, which was heated at 60° C. with stirring. An aqueous solution (1 l) of zinc sulfate (81 g as ZnO) and an aqueous ammonia solution were simultaneously added dropwise to the pure water in the beaker over a period of 30 minutes with care being taken to ensure that the pH of the combined solution remained at 7.5. The resulting precipitate was filtered, washed and dried at 200° C. for 3 hours to obtain a zinc oxide powder. The adsorption characteristics of this zinc oxide powder for various odorous gases are shown in Table 1.

Comparative Example 2

A titanic acid powder was prepared by repeating the procedures of Comparative Example 1 except that the aqueous solution of zinc sulfate was replaced by an aqueous solution of titanium sulfate (80 g as $TiO_2$). The adsorption characteristics of the prepared powder for various odorous gases are shown in Table 1.

Comparative Example 3

The adsorption characteristics of a commercial grade of activated carbon (specific surface area = 1,200 $m^2/g$) for various odorous gases are shown in Table 1.

TABLE 1

| Run No. | Composition (molar ratio) | BET ssa* ($m^2/g$) | X-ray analysis | hydrogen sulfide (10,000**) | ammonia (10,000**) | trimethyl-amine (10,000**) | ethyl mercaptan (5,000) | aceto-aldehyde (1,000) |
|---|---|---|---|---|---|---|---|---|
| Ex. 1 | ZnO:$TiO_2$ = 1.0:9.0 | 410 | amorphous | 1.3 | 60 | — | 600 | — |
| 2 | ZnO:$TiO_2$ = 1.9:8.1 | 400 | amorphous | 0.9 | 20 | — | 13 | — |
| 3 | ZnO:$TiO_2$ = 2.8:7.2 | 400 | amorphous | 0 | 10 | — | 0.7 | — |
| 4 | ZnO:$TiO_2$ = 3.8:6.2 | 360 | amorphous | 0 | 0 | 0 | 0.5 | 2 |
| 5 | ZnO:$TiO_2$ = 4.8:5.2 | 300 | amorphous | 0 | 15 | 0 | 0.3 | 3 |
| 6 | ZnO:$TiO_2$ = 5.6:4.4 | 240 | ZnO | 0 | 30 | 0 | 0.2 | — |
| 7 | ZnO:$TiO_2$ = 6.5:3.5 | 170 | ZnO | 0 | 80 | — | 0.5 | — |
| 8 | ZnO:$TiO_2$ = 7.3:2.7 | 110 | ZnO | 0 | 270 | — | 2 | — |
| 9 Comp. | ZnO:$TiO_2$ = 8.5:1.5 | 90 | ZnO | 0 | 600 | — | 10 | — |

TABLE 1-continued

| Run No. | Composition (molar ratio) | BET ssa* ($m^2/g$) | X-ray analysis | Gas concentration (ppm) after 2 hours of adsorption | | | | |
|---|---|---|---|---|---|---|---|---|
| | | | | hydrogen sulfide (10,000**) | ammonia (10,000**) | trimethyl- amine (10,000**) | ethyl mercaptan (5,000) | aceto- aldehyde (1,000) |
| Ex. 1 | zinc oxide | 30 | | 2.5 | 5,800 | — | 3,500 | — |
| 2 | titanic acid | 420 | | 8,000 | 830 | — | 5,000 | — |
| 3 | activated carbon | 1200 | | 2.5 | 550 | 0 | 0.6 | 9 |

*specific surface area
**Initial concentrations in ppm

What is claimed is:

1. A process for producing a white colored deodorizer consisting essentially of titanium dioxide and zinc oxide, where the molar ratio of $TiO_2$ to ZnO is in the range of from 1:9 to 9:1, the process consisting essentially of the following steps:
    combining an aqueous alkaline solution with a mixed aqueous solution containing a water-soluble zinc compound and a water-soluble titanium compound, said combining step being performed by simultaneous addition of the two solutions in such a way that the combined solution will keep its pH in the range of 6 to 12 and said combining step is performed at a temperature of 20° C. to 80° C.;
    separating the resulting precipitate from the combined solution; and
    drying the separated precipitate at 100° C. to 400° C. to form a white fine powder consisting essentially of $TiO_2$ and ZnO.

2. A process according to claim 1 wherein the molar ratio of $TiO_2$ to ZnO is in the range of from 3:7 to 7:3.

* * * * *

UNITED STATES PATENT AND TRADEMARK OFFICE
CERTIFICATE OF CORRECTION

PATENT NO. : 5,108,739
DATED : April 28, 1992
INVENTOR(S) : Kurihari et al.

It is certified that error appears in the above-identified patent and that said Letters Patent is hereby corrected as shown below:

On the title page: Item

[73] Assignee: change "Ube" to --Ube-shi, Yamaguchi-ken--.

[57] ABSTRACT, line 1, change "titanium oxide" to --titanium dioxide--.

Column 1, line 32, after "inexpensive" change the colon to a semicolon.

Column 2, line 18, change "titanium oxide" to --titanium dioxide--.

Column 3, line 44, change "5-1" to --5-1 (liter)--; and change "1 1" to --1 1 (liter--.

Column 3, line 46, change "(2 1)" to --(2 1) (liter)--.

Column 4, line 30, change "5-1" to --5-1 (liter)--; and change "1 1" to --1 1 (liter)--.

Column 4, line 32, change "(1 1)" to --(1 1) (liter)--.

UNITED STATES PATENT AND TRADEMARK OFFICE
CERTIFICATE OF CORRECTION

PATENT NO. : 5,108,739

DATED : April 28, 1992

INVENTOR(S) : Kurihari et al.

It is certified that error appears in the above-identified patent and that said Letters Patent is hereby corrected as shown below:

Column 4, line 56, in Table I, in the column heading, change "concentration" to --concentrations--.

Column 5, line 2, in Table I, in the column heading, change "concentration" to --concentrations--.

Signed and Sealed this

Twenty-fourth Day of August, 1993

Attest:

BRUCE LEHMAN

Attesting Officer

Commissioner of Patents and Trademarks